United States Patent
Park et al.

(10) Patent No.: US 10,472,660 B2
(45) Date of Patent: Nov. 12, 2019

(54) METHOD FOR PREPARING REBAUDIOSIDE A FROM STEVIOSIDE

(71) Applicant: CJ CHEILJEDANG CORPORATION, Seoul (KR)

(72) Inventors: Sung Hee Park, Seoul (KR); Jung Eun Kim, Bucheon-si (KR); Ran Young Yoon, Suwon-si (KR); Young Ho Hong, Suwon-si (KR); Seong Bo Kim, Seoul (KR); Seung Won Park, Yongin-si (KR)

(73) Assignee: CJ CHEILJEDANG CORPORATION, Seoul (KR)

( * ) Notice: Subject to any disclaimer, the term of this patent is extended or adjusted under 35 U.S.C. 154(b) by 0 days.

(21) Appl. No.: 14/770,962

(22) PCT Filed: Dec. 9, 2013

(86) PCT No.: PCT/KR2013/011330
§ 371 (c)(1),
(2) Date: Aug. 27, 2015

(87) PCT Pub. No.: WO2014/133248
PCT Pub. Date: Sep. 4, 2014

(65) Prior Publication Data
US 2016/0010133 A1    Jan. 14, 2016

(30) Foreign Application Priority Data
Feb. 28, 2013  (KR) .................. 10-2013-0022176

(51) Int. Cl.
*C12P 19/56*    (2006.01)
*C12N 9/10*    (2006.01)
*C07H 15/24*    (2006.01)

(52) U.S. Cl.
CPC ........... *C12P 19/56* (2013.01); *C07H 15/24* (2013.01); *C12N 9/1051* (2013.01); *C12N 9/1062* (2013.01); *C12Y 204/01013* (2013.01)

(58) Field of Classification Search
None
See application file for complete search history.

(56) References Cited

U.S. PATENT DOCUMENTS

| | | | |
|---|---|---|---|
| 4,219,571 A * | 8/1980 | Miyake | C12P 19/18 426/48 |
| 4,590,160 A * | 5/1986 | Nishihashi | C07H 13/06 426/52 |
| 7,884,265 B2 | 2/2011 | Morita et al. | |
| 2010/0099875 A1 | 4/2010 | Stephan et al. | |
| 2011/0087011 A1 | 4/2011 | Chiang et al. | |
| 2011/0256588 A1 | 10/2011 | Lee et al. | |

FOREIGN PATENT DOCUMENTS

| | | | | |
|---|---|---|---|---|
| CN | 102766667 A | * 11/2012 | ............ | C12P 19/56 |
| JP | 11-290075 A | 12/1999 | | |
| JP | 2000-245279 A | 9/2000 | | |
| JP | 2007-330112 A | 12/2007 | | |
| KR | 10-2011-0115699 A | 10/2011 | | |
| WO | WO 2011153378 A1 | * 12/2011 | ........... | A23L 1/2366 |
| WO | WO-2013022989 A2 | * 2/2013 | ........... | C12N 9/0071 |

OTHER PUBLICATIONS

Eng. machine tranlation of Li et al. (Nov. 7, 2012) Method for transforming stevioside into rebaudioside E. Chinese patent application publication No. CN 102766667 A. pp. 1-6. specif. pp. 2, 3, 4.*
Pollock, C.J. 1986. Fructans and the metabolism of sucrose in vascular plants. New Phytology 104: 1-24. specif. pp. 1, 5, 15.*
Guleria, P. et al. 2011. Effect of sucrose on steviol glycoside biosynthesis pathway in Stevia rebaudiana. Asian Journal of Plant Sciences 10(8): 401-407. specif. p. 401.*
Cardini, C.E. et al. 1955. The biosynthesis of sucrose. Journal of Biological Chemistry 214: 149-155. specif. p. 149.*
Humphrey, T.V. et al. 2006. Spatial organisation of four enzymes from Stevia rebaudiana that are involved in steviol glycoside synthesis. Plant Molecular Biology 61:47-62. specif. p. 47.*
Wang, M-B. et al. 1992. A complete sequence of the rice sucrose synthase-1 (RSs1) gene. Plant Molecular Biology 19: 881-885. specif. pp. 881, 883, 884.*
Shibata, H. et al. 1991. Glucosylation of steviol and steviol-glucosides in extracts from Stevia rebaudiana Bertoni. Plant Physiology 95: 152-156. specif. pp. 152, 155.*
Oxford Dictionary of Biochemistry and Molecular Biology. Sucrose synthase.Oxford University Press (publisher). Second edition. Copyright 2006. The General Editors. New York, New York. p. 641.*
Richman et al., "Functional genomics uncovers three glucosyltransferases involved in the synthesis of the major sweet glucosides of *Stevia rebaudiana*," *The Plant Journal*,(41): 56-67, 2005.
Chen et al., "Research Advances in Biosynthesis of UDPG," *China Biotechnology* 32(9):125-130 (2012).
Madhav et al., "Functional and structural variation of uridine diphosphate glycosyltransferase (UGT) gene of *Stevia rebaudiana*-UGTSr involved in the synthesis of rebaudioside A," *Plant Physiology and Biochemistry* 63:245-253 (2013).

* cited by examiner

*Primary Examiner* — Renee Claytor
*Assistant Examiner* — Sharon M. Papciak
(74) *Attorney, Agent, or Firm* — Seed IP Law Group LLP

(57) ABSTRACT

The present invention relates to an in-situ method for preparing rebaudioside A from sucrose and stevioside by sucrose synthase and glycosyltransferase.

4 Claims, 4 Drawing Sheets
Specification includes a Sequence Listing.

METHOD FOR PREPARING REBAUDIOSIDE A FROM STEVIOSIDE

TECHNICAL FIELD

The present invention relates to a method for preparing rebaudioside A from sucrose and stevioside as raw materials by sucrose synthase and glycosyltransferase.

BACKGROUND ART

Stevia is a high potency sweetener more than 200 times as sweet as sugar and is obtained by hot water extraction of *Stevia rebaudiana* Bertoni which belongs to family Compositae. Rebaudioside A is known to have less bitter taste and the most similar sweetening quality to sugar among the sweetening ingredients of stevia extracts and is 400 times sweeter than sugar, and occupies about 20% or so in the extracts in the case of non-modified plants. The most predominant ingredient in the extracts is stevioside which is a precursor to rebaudioside A. In order to produce high purity rebaudioside A, it is necessary to perform improvement of seeds with high content of rebaudioside A, cultivation, harvest, breed management, and the like, which entail economic problems in terms of time and cost.

In order to solve these problems, research has been carried out to convert stevioside into rebaudioside A. Typical examples include a method for converting stevioside into rebaudioside A by binding a glucose molecule to stevioside through enzymatic conversion using beta-1,3-glucanase derived from soil microorganisms (Korean Patent Publication 2004-0026747A and U.S. Pat. No. 6,469,947). Typical examples of sugar donor substrates employed in enzymatic conversion may include curdlan (beta-1,3-glucan). Curdlan is a high cost material with low solubility and has a drawback in that industrial application thereof is difficult. Furthermore, although a report says that curdlan converts stevioside into rebaudioside glycoside through fungal fermentation, the cultivation of the microorganisms takes about 15 days and also produces other steviol glycosides, such as rebaudioside B and the like, which make the conversion rate to final rebaudioside A only around 40%.

DISCLOSURE

Technical Problem

An object of the present invention is to provide a method for preparing rebaudioside A with high production efficiency by overcoming restriction of low production rate for rebaudioside A in microorganism-derived enzymatic conversion.

Another object of the present invention is to provide a method for preparing rebaudioside A with high industrial applicability since the preparation procedure is simple, cost saving and less time consuming.

Technical Solution

In accordance with one aspect of the present invention, there is provided a method for preparing rebaudioside A, including:

(1) reacting sucrose and nucleotide diphosphate in the presence of sucrose synthase to prepare nucleotide diphosphate to which glucose is bonded; and (2) reacting the nucleotide diphosphate to which glucose is bonded with stevioside in the presence of glycosyltransferase to prepare rebaudioside A.

In accordance with another aspect of the present invention, there is provided an in-situ method for preparing rebaudioside A from stevioside, including: reacting sucrose, nucleotide diphosphate, stevioside, sucrose synthase and glycosyltransferase to prepare rebaudioside A.

In accordance with a further aspect of the present invention, there is provided rebaudioside A prepared by the method for preparing rebaudioside A according to the present invention.

Advantageous Effects

The method for preparing rebaudioside A according to the present invention provides rebaudioside A with high purity having almost no side-products, and high yield.

The method for preparing rebaudioside A according to the present invention is suitable for mass production since it is economical due to the use of inexpensive raw materials, and the procedure is simple and less time consuming.

DESCRIPTION OF DRAWINGS

In FIG. 1, (a) shows the presence of stevioside (1) only at reaction time of 0 hours, (b) shows that uridine diphosphate (2) to which glucose is bonded is produced by sucrose synthase after the completion of reaction time of 1 hour.

In FIG. 2, (a) shows the presence of stevioside (1) only at reaction time of 0 hours, (b) shows that both stevioside (1) and rebaudioside A (2) are present after a reaction time of 0.5 hour, and (c) shows that all stevioside (1) is converted into rebaudioside A (2) after a reaction time of 1 hour.

In FIG. 3, (a) shows the presence of stevioside (1) only at reaction time of 0 hours when stevioside substrate concentration is 100 mM, (b) shows the presence of rebaudioside A (2) only after a reaction time of 24 hours when stevioside substrate concentration is 100 mM, and (c) shows the presence of both stevioside (1) and rebaudioside A (2) after a reaction time of 24 hours when stevioside substrate concentration is 250 mM.

BEST MODE

Figure 1:
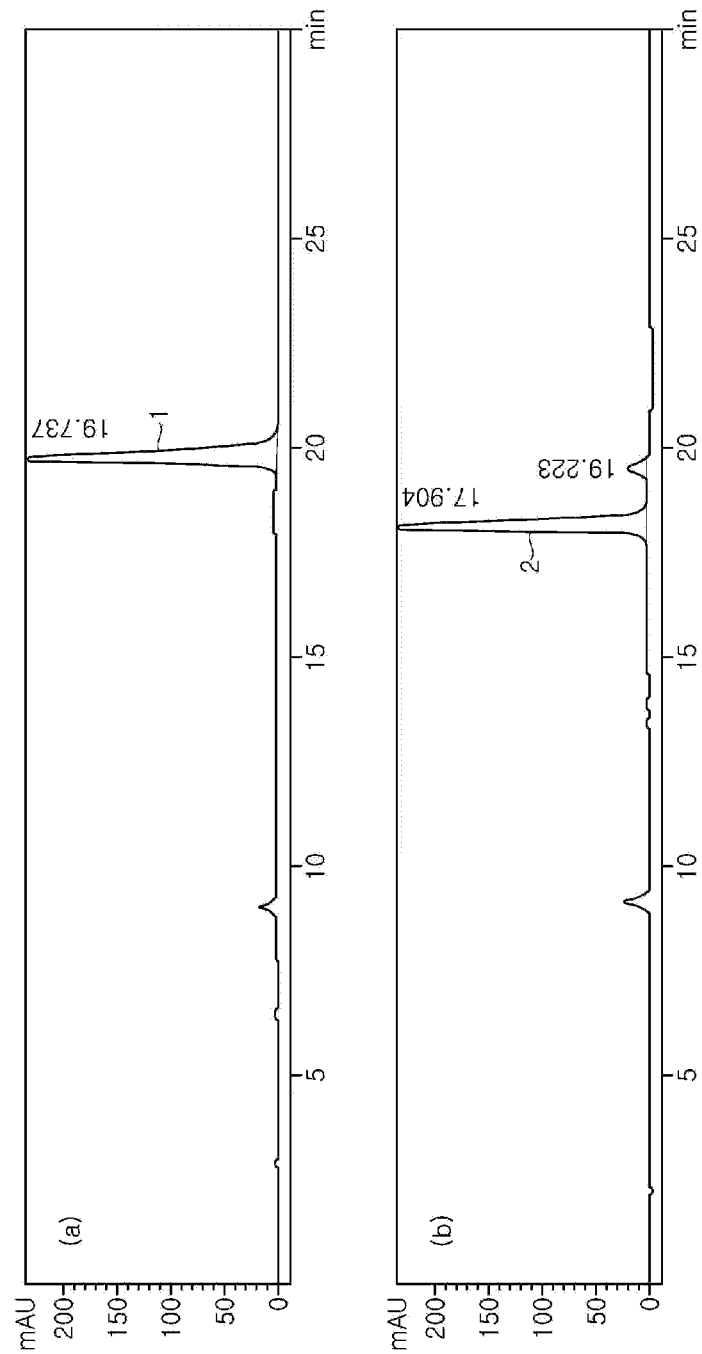
FIG. 1 shows HPLC analysis results, demonstrating that fructose and uridine diphosphate to which glucose is bonded are produced by sucrose synthase.

One embodiment of the present invention relates to a method for preparing rebaudioside A, including:

(1) reacting sucrose and nucleotide diphosphate in the presence of sucrose synthase to prepare nucleotide diphosphate to which glucose is bonded; and (2) reacting the nucleotide diphosphate to which glucose is bonded with stevioside in the presence of glycosyltransferase to prepare rebaudioside A. The steps (1) and (2) are performed in-situ sequentially or consecutively, preferably in-situ consecutively.

Another embodiment of the present invention relates to a method for preparing rebaudioside A from stevioside, including: reacting sucrose, nucleotide diphosphate, stevioside, sucrose synthase and glycosyltransferase to prepare rebaudioside A. The reaction of sucrose, nucleotide diphosphate, stevioside, sucrose synthase and glycosyltransferase may be performed in-situ.

The term "in-situ" used herein means that a reaction is consecutively performed in a single reaction system.

Sucrose synthase plays a role in the production of sucrose by reversibly transferring glucose, which is bonded to nucleotide diphosphate, to fructose in plant sugar catabolism. In the present invention, sucrose synthase demonstrates activity to separate nucleotide diphosphate to which glucose is bonded and fructose by reacting sucrose and nucleotide diphosphate in the range of pH 5 to pH 10.

[Chemical Reaction 1]

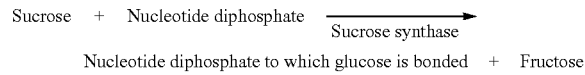

Sucrose + Nucleotide diphosphate →(Sucrose synthase) Nucleotide diphosphate to which glucose is bonded + Fructose Nucleotide diphosphate to which glucose is bonded can be reacted with stevioside by means of glycosyltransferase to produce rebaudioside A.

[Chemical Reaction 2]

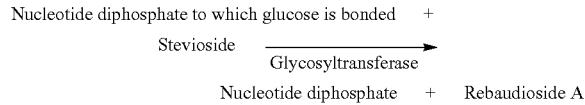

Nucleotide diphosphate to which glucose is bonded + Stevioside →(Glycosyltransferase) Nucleotide diphosphate + Rebaudioside A Chemical Reactions 1 and 2 in the present invention may be performed sequentially in separate reactors, but are preferably performed consecutively in one reactor.

In the present invention, Chemical Reactions 1 and 2 may be combined into one reaction formula below:

[Chemical Reaction 3]

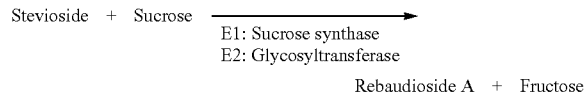

Stevioside + Sucrose →(E1: Sucrose synthase, E2: Glycosyltransferase) Rebaudioside A + Fructose The present invention provides a consecutive reaction system, wherein one glucose is specifically bonded to the C-3' position of stevioside 13-O-glucose to synthesize rebaudioside A with high yield in accordance with Chemical Reaction 3 above.

In the present invention, sucrose synthase may be derived from rice, corn, wheat, bamboo, Arabidopsis thaliana, grass, barley, sorghum or potato. Preferably, sucrose synthase is derived from rice, corn, wheat, or barley, particular preferably from rice, especially Oryza sativa. Sucrose synthase may be produced from recombinant Escherichia coli, Bacillus, yeast, Corynebacterium or Agrobacterium transformed with a vector containing a sucrose synthase gene. Sucrose synthase may be further purified after it is produced from Escherichia coli and the like. Sucrose synthase is well known in the art. Although it is not particularly limited, sucrose synthase may include a base sequence shown in SEQ ID NO: 3.

In the present invention, sucrose is not particularly limited so long as it can serve as a substrate for sucrose synthase to provide glucose to nucleotide diphosphate. Examples of sucrose may include raw sugar or sugar.

In the present invention, purine or pyrimidine may be used as the nucleotide diphosphate. Preferably, uridine diphosphate is used as the nucleotide diphosphate.

In the present invention, the reaction temperature in step (1) or Chemical Reaction 1 may be 20° C. to 60° C., and the reaction pH may be in the range of pH 5 to pH 10. Preferably, the reaction temperature is 30° C. to 55° C. and the reaction pH is in the range of pH 6 to pH 9, particular preferably the reaction temperature is 35° C. to 50° C. and the reaction pH is in the range of pH 7 to pH 8. In the present invention, the reaction time in step (1) or Chemical Reaction 1 is 30 minutes to 48 hours, preferably 1 hour to 36 hours, particular preferably 1 hour to 24 hours, without being limited thereto.

In the present invention, glycosyltransferase may be derived from Oryza sativa, Stevia rebaudiana Bertoni, Bambusa oldhamii, Brachypodium distachyon, Hordeum vulgare, Sorghum bicolor, Zea mays, or Arabidopsis thaliana. Preferably, glycosyltransferase is derived from Oryza sativa, Stevia rebaudiana Bertoni, or Bambusa oldhamii. Particular preferably, glycosyltransferase is derived from Stevia rebaudiana Bertoni. Glycosyltransferase may be produced from recombinant Escherichia coli, Bacillus, yeast, Corynebacterium or Agrobacterium transformed with a vector containing a glycosyltransferase gene. Glycosyltransferase may be further purified after it is produced from Escherichia coli and the like. Glycosyltransferase is well known in the art. Although it is not particularly limited, glycosyltransferase may include a base sequence shown in SEQ ID NO: 4.

In the present invention, stevioside is hot water or aqueous ethanol solution extract from Stevia rebaudiana, or purified material thereof, or a by-product after the production of rebaudioside A from the extract. Stevioside may be used in an amount of 10 wt % or more, preferably 50 wt % or more, particularly preferably 70 wt % or more, more particular preferably 80 wt % or more, based on total weight of steviol glycoside.

In the present invention, the reaction temperature in step (2) or Chemical Reaction 2 may be 20° C. to 60° C., and the reaction pH may be in the range of pH 5 to pH 10. Preferably, the reaction temperature is 30° C. to 55° C., and the reaction pH is in the range of pH 6 to pH 9. Particular preferably, the reaction temperature is 35° C. to 50° C., and the reaction pH is in the range of pH 7 to pH 8. In the present invention, the reaction time in step (2) or Chemical Reaction 2 may be 30 minutes to 48 hours, preferably 1 hour to 36 hours, particular preferably 1 hour to 24 hours, without being limited thereto.

In the present invention, the reaction temperature for the step of preparing rebaudioside A by reacting sucrose, nucleotide diphosphate, stevioside, sucrose synthase and glycosyltransferase in-situ may be 20° C. to 60° C., and the reaction pH may be in the range of pH 5 to pH 10. Preferably, the reaction temperature is 30° C. to 55° C., and the reaction pH is in the range of pH 6 to pH 9. Particular preferably, the reaction temperature is 35° C. to 50° C., and the reaction pH is in the range of pH 7 to pH 8.

In the present invention, purine or pyrimidine may be used as the nucleotide diphosphate. Preferably, uridine diphosphate is used as the nucleotide diphosphate.

Another embodiment of the present invention provides rebaudioside A prepared by a method described herein.

Rebaudioside A according to the present invention is characterized in that it is produced by using entire amount of stevioside residing in steviol glycoside. Such characteristics can allow stevioside content in the glycoside to be 5 wt % or less, preferably 3 wt % or less, particularly preferably 1 wt % or less, thereby capable of omitting a step of separating stevioside from rebaudioside A in a purification process, which leads to cost-savings. In addition, in case that only a small amount of rebaudioside A is present as glycoside besides stevioside in the raw materials as in the present invention, the preparation method has a merit that a high purity product wherein rebaudioside A content in steviol glycoside through enzymatic conversion is 99% or more. Furthermore, sucrose that is used as a sugar donor in the present invention can be purchased at 50 times lower cost than curdlan used as a raw material in the prior inventions. As a result, the present invention is capable of producing rebaudioside A with high purity at low cost/high efficiency as compared to the prior art.

Hereinafter, the present invention will be described in more detail with reference to the following examples. It should be understood that these examples are provided for illustration only and are not to be construed in any way as limiting the present invention.

Example 1

Gene Collection and Recombinant Protein Production

1) Preparation of Sucrose Synthase Gene Recombinant *Escherichia coli*

Primers used in PCR (Polymerase Chain Reaction) had restriction enzyme recognition sequences for NdeI and HindIII that react respectively with a partial base sequence of both ends of sucrose synthase.

```
(FORWARD)  5'-CATATGGCTGCCAAGCTAGCTCG-3'
(BACKWARD) 5'-AAGCTTTTACTTGGATGTGCTCTCTC-3'
```

For gene amplification, the isothermal amplification procedure repeated 30 cycles consisting of denaturing at 94° C. for 30 seconds, annealing at 60° C. for 30 seconds, and extension at 72° C. for 2 minutes, thereby obtaining about 2.5 kb of PCR product.

The obtained cDNA fragment was inserted into a pET-28a(+) vector and transformed into *Escherichia coli* BL21 (DE3). The transformed *Escherichia coli* were streaked onto plate media containing kanamycin to initially select kanamycin resistant strains. The selected strains were subjected to liquid cultivation, followed by purification of DNAs. Finally, when DNAs were doubly cleaved with NdeI and HindIII, a strain confirmed to have about 2.5 kb of DNA fragment was selected. As a result of base sequence analysis using an automated DNA Sequencer, the base sequence (SEQ ID NO: 1) of sucrose synthase gene obtained in the present invention was identical to that of the reported sucrose synthase gene below:

```
                                              SEQ ID NO: 1
TGCCAACAATCGCAACATGCCATGGTGGCCCTGCTGAGATTATTGTTGAT

GGGGTGTCTGGTCTGCACATTGATCCTTACCACAGTGACAAGGCTGCTGA

TATCTTGGTCAACTTCTTTGAAGAAGTGCAAGCAGGATTCAACCTACTGGG
```

```
                                              -continued
ACAATATTTCACAGGGAGGTCTGCAGAGGATTTACGAGAAGTACACCTGG

AAGCTGTACTCTGAGAGGCTGATGACCTTGACTGGTGTATACGGATTCTG

GAAGTACGTAAGCAACCTTGAGAGGCGCGAGACTCGCCGTTACATTGAGA

TGTTCTATGCTCTGAAATACCGCAGCCTGGCCAGCGCCGTCCCATTGGCT

GTCGATGGAGAGAGCACATCCAAGTAA
```

2) Preparation of Glycosyltransferase Gene Recombinant *Escherichia coli*

Primers used in PCR had restriction enzyme recognition sequences for NdeI and HindIII that react respectively with a partial base sequence of both ends of glycosyltransferase gene derived from *Stevia rebaudiana*.

```
(FORWARD)  5'-CATATGGAAAATAAAACGGA-3'
(BACKWARD) 5'-AAGCTTTTACAACGATGAAATGT-3'
```

For gene amplification, the isothermal amplification procedure was repeated for 30 cycles consisting of denaturing at 94° C. for 30 seconds, annealing at 60° C. for 30 seconds, and extension at 72° C. for 2 minutes, thereby obtaining about 1.4 kb of PCR product. The obtained cDNA fragment was inserted into a pET-28a(+) vector and transformed into *Escherichia coli* BL21(DE3). The transformed *Escherichia coli* were streaked onto plate media containing kanamycin to initially select kanamycin resistant strains. The initially selected strains were subjected to liquid cultivation, followed by purification of DNAs. Finally, when DNAs were doubly cleaved with NdeI and HindIII, a strain confirmed to have about 1.4 kb of DNA fragment was selected. As the result of base sequence analysis using an automated DNA Sequencer, the base sequence (SEQ ID NO: 2) of glycosyltransferase gene obtained in the present invention was identical to that of the reported glycosyltransferase gene below:

```
                                              SEQ ID NO: 2
AGAAGTGCTAGCTCATGGAGCAATAGGCGCATTCTGGACTCATAGCGGAT

GGAACTCTACGTTGGAAAGCGTTTGTGAAGGTGTTCCTATGATTTTCTCG

GATTTTGGGCTCGATCAACCGTTGAATGCTAGATACATGAGTGATGTTTT

GAAGGTAGGGGTGTATTTGGAAAATGGGTGGGAAAGAGGAGAGATAGCAA

ATGCAATAAGAAGAGTTATGGTGGATGAAGAAGGAGAATACATTAGACAG

AATGCAAGAGTTTTGAAACAAAAGGCAGATGTTTCTTTGATGAAGGGTGG

TTCGTCTTACGAATCATTAGAGTCTCTAGTTTCTTACATTTCATCGTTGT

AA
```

3) Production of Recombinant Protein

A test tube containing 5 ml of LB medium was inoculated with lyophilized recombinant *Escherichia coli* BL21(DE3), followed by seed culturing in an incubator at 37° C. until the absorbance at 600 nm became 2.0. The seed cultured solution was added to a 2000 ml flask containing 500 ml of LB medium and then cultured. Further, 0.1 mM IPTG (isopropyl β-D-1-thiogalacthiopyranoside) was added until the absorbance at 600 nm became 0.4, thereby inducing mass expression of sucrose synthase and glycosyltransferase, respectively. The culture conditions were adjusted so that the stirring speed was 180 rpm and the culture temperature was 37° C. during the procedure, while the stirring speed was 120 rpm and the culture temperature was 16° C. after the addition of IPTG. The culture solution of the transformed strain was centrifuged at 6,000 g at 4° C. for 20 minutes, followed by washing twice with 50 mM Tris-hydrochloric acid buffer, then adding 50 mM Tris-hydrochloric acid buffer, pH 7.5 in order to lyse the cell solution with a sonicator. The cell lysate was centrifuged again at 13,000 g at 4° C. for 20 minutes to separate a cell supernatant as an enzyme solution. In order to exactly identify properties of enzymes, the enzyme solution was purified using a Ni-NTA superflow column. The molecular weight of the purified enzyme was measured by SDS-PAGE. As a result, it was confirmed that sucrose synthase derived from rice (*Oryza sativa*) had a length of 92 kDa (SEQ ID NO: 3) and glycosyltransferase (UDP-glycosyltransferase) derived from stevia (*Stevia rebaudiana*) had a length of 57 kDa (SEQ ID NO: 4).

Example 2

Measurement of Enzyme Activity Using HPLC
1) Measurement of Sucrose Synthase Activity
The activity of sucrose synthase derived from rice (*Oryza sativa*) was measured by means of HPLC. Analysis conditions for HPLC to measure the activity of sucrose synthase derived from rice (*Oryza sativa*) were as follows:
Conditions for HPLC Analysis
Detector Wavelength: 260 nm
Flow rate: 1 ml/min
Sample injection vol.: 10 μl
Column: C18 4.6×250 mM (5 μm pore size)
Solvent: A: 8 mM Tetrabutylammonium persulfate in 100 mM potassium phosphate [pH 5.3]
B: 70% solvent A+30% Methanol
The total analysis time was set to 30 minutes, wherein the analysis started the gradient with 100% solvent A, at run time of 15 minutes the gradient of solvent B was increased to 20%, and then at run time of 17 minutes the gradient returned to 100% solvent A.

The activity of sucrose synthase derived from rice (*Oryza sativa*) was confirmed by enzymatic reaction to see if raw sugar or sugar (sucrose) and uridine diphosphate were reacted to produce uridine diphosphate to which glucose was bonded. The conditions for enzyme reactions were as follows:

100 mM sucrose, 10 mM uridine diphosphate and 0.1 mg/ml sucrose synthase prepared in Example 1-3) in 50 mM phosphate buffer (pH 6.5) were subjected to enzymatic reaction at 37° C. for 1 hour. After heating to 100° C. for 5 minutes to stop the reaction, HPLC analysis was performed to measure the produced amount of uridine diphosphate to which glucose was bonded. As a result, it was confirmed that uridine diphosphate was converted into uridine diphosphate to which glucose was bonded, indicating 90% conversion as compared to initial molar concentration (FIG. 1). In FIG. 1, (a) shows that only uridine diphosphate (1) is present at reaction time of 0 hours, (b) shows that uridine diphosphate to which glucose is bonded (2) is produced by means of sucrose synthase after the completion of reaction time of 1 hour.

2) Measurement of Glycosyltransferase Activity
The conditions for HPLC analysis to measure glycosyltransferase (UDP-glycosyltransferase) derived from stevia (*Stevia rebaudiana*) were as follows:
Conditions for HPLC Analysis
Detector Wavelength: 210 nm
Flow rate: 1 ml/min
Sample injection vol.: 10 μl
Column: C18 4.6×250 mM (5 μm pore size)
Solvent: Acetonitrile:10 mM sodium phosphate [pH 2.6]=32:68

Figure 2:
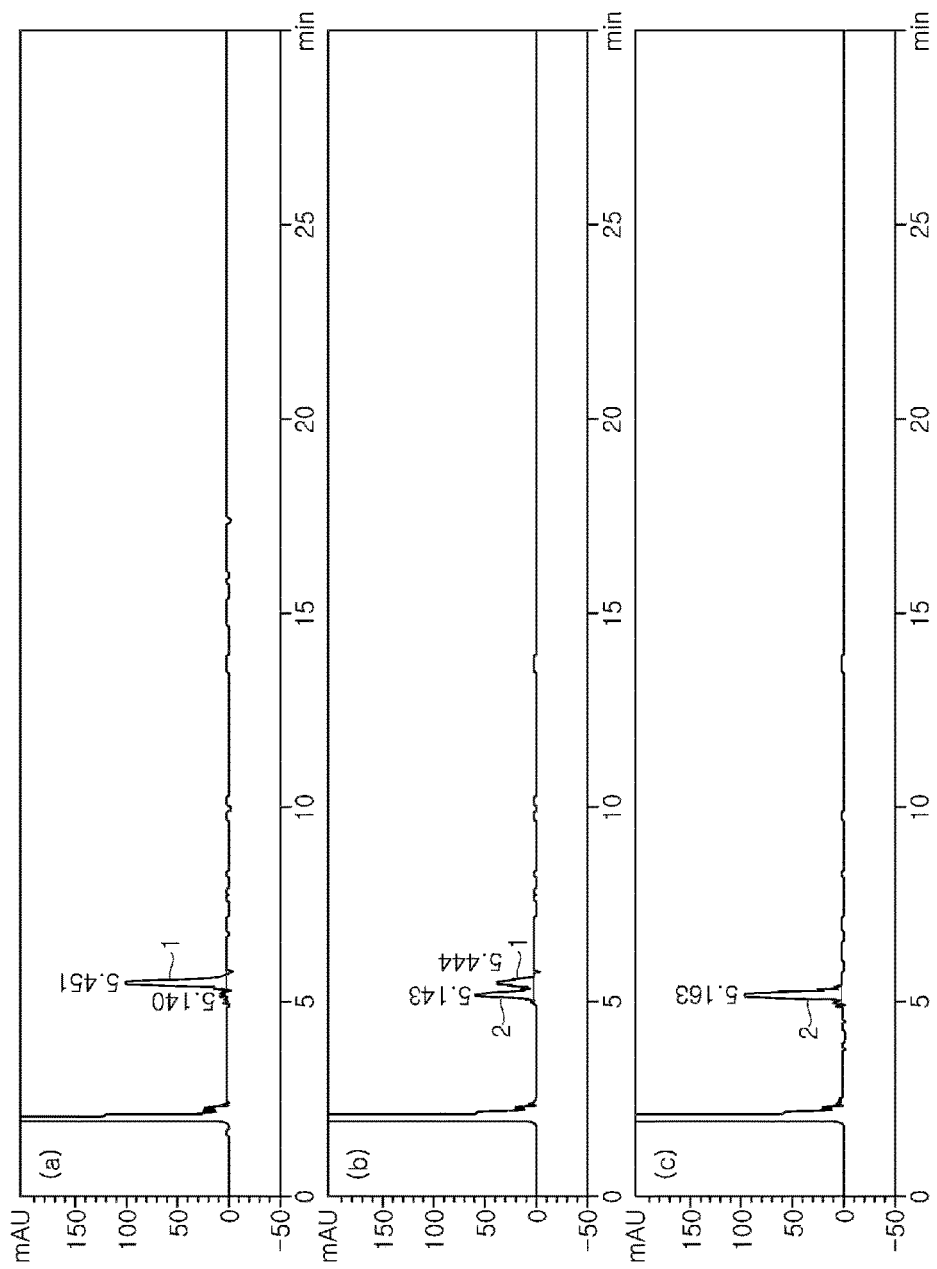
FIG. 2 shows HPLC analysis results, demonstrating that stevioside is converted into rebaudioside A by glycosyltransferase.

The activity of glycosyltransferase (UDP-glycosyltransferase) derived from stevia (*Stevia rebaudiana*) was confirmed by enzymatic conversion to see if bonding one molecule of glucose to stevioside leads to conversion to rebaudioside A. The conditions for enzymatic reaction were as follows: 2 mM stevioside (>96%), 10 mM uridine diphosphate glucose, and 0.1 mg/ml glycosyltransferase derived from stevia prepared in Example 1-3) in 50 mM phosphate buffer (pH 7.0) were subjected to enzymatic reaction at 37° C. for one hour. Stevioside used as a substrate for enzymatic reaction was pure stevioside with purity of 96% or more. A mixed specimen containing about 3% of rebaudioside A was used as a standard material before and after reaction at the time of HPLC analysis. The enzyme reaction was stopped by heating to 100° C. for 5 minutes, followed by performing HPLC to measure the produced amount of rebaudioside A. As an analysis result, it was confirmed that stevioside was converted into rebaudioside A with 100% conversion as compared to molar concentration (FIG. 2). FIG. 2 shows HPLC analysis results, demonstrating that stevioside is converted into rebaudioside A by glycosyltransferase. In FIG. 2, (a) shows the presence of stevioside (1) only at reaction time of 0 hours, (b) shows that both stevioside (1) and rebaudioside A (2) are present after a reaction time of 0.5 hours, and (c) shows that all stevioside (1) is converted into rebaudioside A (2) after a reaction time of 1 hour.

Example 3

Measurement of Conversion Rate from Stevioside to Rebaudioside A by In-Situ Reaction of Sucrose Synthase and Glycosyltransferase The conversion rate from stevioside to rebaudioside A was confirmed by in-situ reaction of sucrose synthase and glycosyltransferase (UDP-glycosyltransferase). The conditions for enzymatic reactions were as follows:

Enzymatic reactions were performed using 50 mM phosphate buffer (pH 6.5) containing 1M sucrose, 20 mM uridine diphosphate, 100~250 mM stevioside and 0.1 mg/ml of sucrose synthase prepared in Example 1-3) and 0.1 mg/ml of glycosyltransferase prepared in Example 1-3) at a temperature of 45° C. for 24 hours. The substrate used in the present invention was the stevioside mixture specified in Example 2. After completion of the reactions, the reactions were stopped by heating to 100° C. for 5 minutes. After that, HPLC analysis was performed to measure the concentration of produced rebaudioside A depending on the concentration of stevioside. The conversion rate from stevioside to rebaudioside A was calculated from the molar concentration of rebaudioside A produced as compared to molar concentration of stevioside used (FIG. 3 and Table 1 (Conversion rate after reaction for 24 hours)).

TABLE 1

| Concentration of stevioside (mM) | Conversion rate (%) |
|---|---|
| 100 | 100 |
| 150 | 63.90 |
| 200 | 56.72 |
| 250 | 39.96 |

Figure 3:
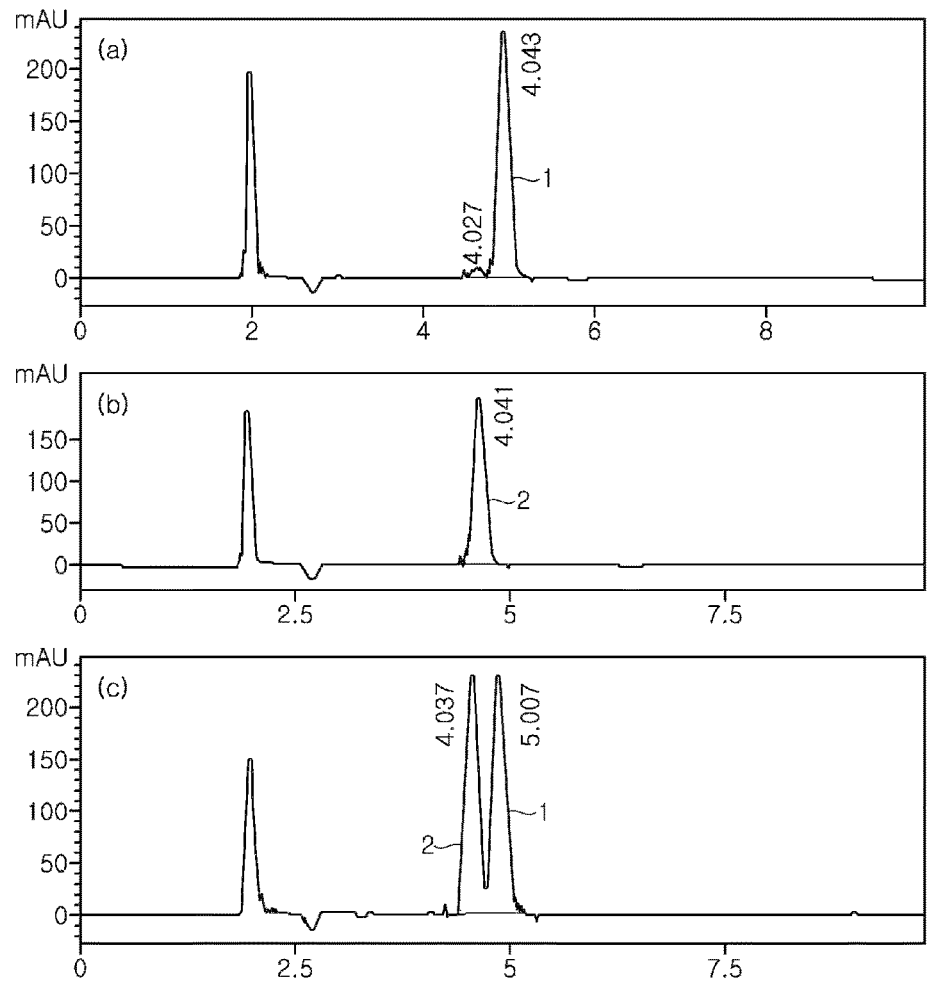
FIG. 3 shows HPLC analysis results, demonstrating that rebaudioside A (2) is produced from stevioside (1) by sucrose synthase and glycosyltransferase.

FIG. 3 shows HPLC analysis results, demonstrating that rebaudioside A (2) is produced from stevioside (1) by sucrose synthase and glycosyltransferase. In FIG. 3, (a) shows the presence of stevioside (1) only at reaction time of 0 hours when the substrate concentration is 100 mM, (b) shows the presence of rebaudioside A (2) only after a reaction time of 24 hours when the substrate concentration is 100 mM, and (c) shows the presence of both stevioside (1) and rebaudioside A (2) after a reaction time of 24 hours when the substrate concentration is 250 mM.

Example 4 pH Stability in In-Situ Reaction of Sucrose Synthase and Glycosyltransferase

Uridine diphosphate to which glucose was bonded produced by sucrose synthase derived from rice (*Oryza sativa*) was converted into rebaudioside A by reacting with stevioside by glycosyltransferase, dissociating uridine diphosphate. When the two sorts of enzymes were present in a single reactor and rebaudioside A was produced, the optimum pH was checked. The conditions for HPLC analysis for measuring the optimum pH are as follows:

Condition for HPLC Analysis
Detector Wavelength: 210 nm
Flow rate: 1 ml/min
Sample injection vol.: 10 μl
Column: C18 4.6×250 mM (5 μm pore size)
Solvent: Acetonitrile:10 mM sodium phosphate [pH 2.6]=32:68

Figure 4:
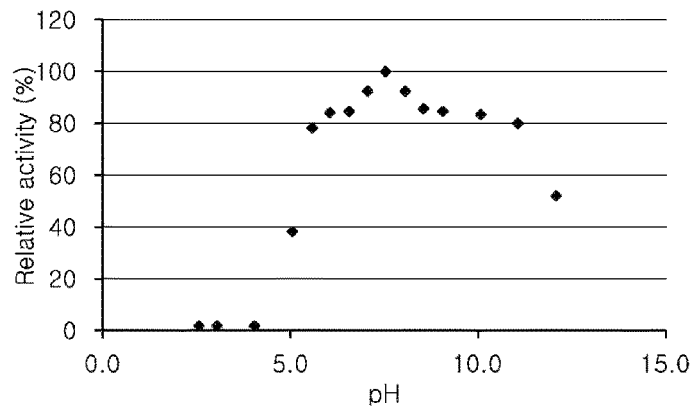
FIG. 4 shows a graph demonstrating the results of appropriate pH evaluation for sucrose synthase and glycosyltransferase.

The optimum pH was confirmed through complex reaction of sucrose synthase and glycosyltransferase (UDP-glycosyltransferase). Conditions for enzymatic reactions were as follows: Enzymatic reactions were performed by using 50 mM phosphate buffer (pH 6.5) containing 1M sucrose, 200 mM uridine diphosphate, 40 mM stevioside and 0.1 mg/ml of sucrose synthase prepared in Example 1-3) and 0.1 mg/ml of glycosyltransferase prepared in Example 1-3) at a temperature of 45° C. for 24 hours. As a pH 2.5 to pH 12.0 buffer, Universal buffer was used. The reactions were stopped by heating to 100° C. for 5 minutes. After that, HPLC analysis was performed to measure the production rate of rebaudioside A. By comparing the produced amount of rebaudioside A, the reaction pH for the reaction system showing maximum value was deemed to be an optimum pH for the complex reaction. The optimum pH for the complex reaction of sucrose synthase and glycosyltransferase was confirmed to be approximately pH 7.5 μm a reaction carried out at a temperature of 45° C. for 60 minutes (FIG. 4 and Table 2).

TABLE 2

| pH | Enzyme relative activity (%) |
|---|---|
| 2.5 | 2.99 |
| 3.0 | 2.85 |
| 4.0 | 2.66 |
| 5.0 | 38.55 |
| 5.5 | 78.66 |
| 6.0 | 84.54 |
| 6.5 | 85.45 |
| 7.0 | 93.24 |
| 7.5 | 100 |
| 8.0 | 93.04 |
| 8.5 | 86.42 |
| 9.0 | 85.12 |
| 10.0 | 84.01 |
| 11.0 | 80.47 |
| 12.0 | 52.34 |

Example 4

Temperature Stability in an In-Situ Reaction of Sucrose Synthase and Glycosyltransferase Uridine diphosphate to which glucose was bonded produced by sucrose synthase derived from rice (*Oryza sativa*) was converted into rebaudioside A by reacting with stevioside by glycosyltransferase, dissociating uridine diphosphate. When the two sorts of enzymes were present in a single reactor and rebaudioside A was produced, the optimum temperature was checked. The conditions for HPLC analysis for measuring the optimum temperature were as follows:

Conditions for HPLC Analysis
Detector Wavelength: 210 nm
Flow rate: 1 ml/min
Sample injection vol.: 10 μl
Column: C18 4.6×250 mM (5 μm pore size)
Solvent: Acetonitrile:10 mM sodium phosphate [pH 2.6] =32:68

Figure 5:
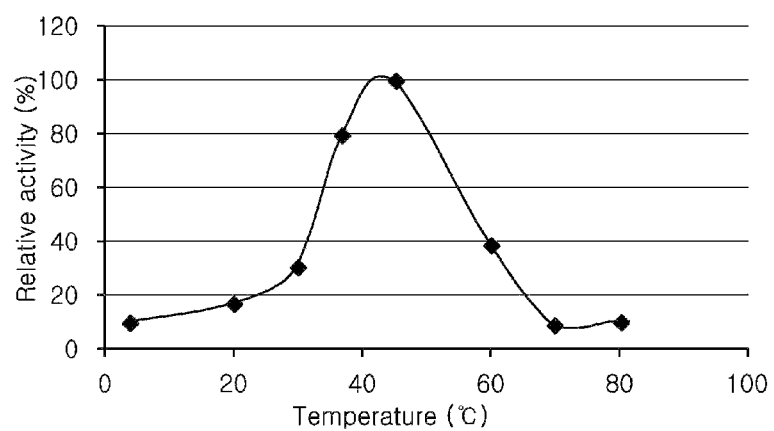
FIG. 5 shows a graph demonstrating the results of appropriate temperature evaluation for sucrose synthase and glycosyltransferase.

The optimum temperature was confirmed through a complex reaction of sucrose synthase and glycosyltransferase (UDP-glycosyltransferase). The conditions for enzymatic reactions were as follows: Enzymatic reactions were performed by using 50 mM phosphate buffer (pH 6.5) containing 1M sucrose, 200 mM uridine diphosphate, 40 mM stevioside and 0.1 mg/ml of sucrose synthase and 0.1 mg/ml of glycosyltransferase at temperatures of 4° C., 20° C., 30° C., 37° C., 45° C., 60° C., 70° C., and 80° C. The reactions were stopped by heating to 100° C. for 5 minutes. After that, HPLC analysis was performed to measure the production rate of rebaudioside A. By comparing the produced amount of rebaudioside A, the reaction temperature for the reaction system showing maximum value was deemed to be an optimum temperature for the complex reaction. The optimum temperature for the complex reaction of sucrose synthase and glycosyltransferase was confirmed to be approximately 45° C. in a reaction carried out at pH 6.5 for 60 minutes. Relative enzyme activity is summarized in FIG. 5 and Table 3.

TABLE 3

| Temperature (° C.) | Relative enzyme activity (%) |
|---|---|
| 4 | 10.19 |
| 20 | 17.20 |
| 30 | 31.21 |
| 37 | 80.48 |
| 45 | 100 |
| 60 | 39.24 |
| 70 | 9.71 |
| 80 | 10.40 |

The invention claimed is:

1. A method for preparing rebaudioside A from stevioside, comprising performing in a single reaction system the following two reactions:
   (1) reacting sucrose and nucleotide diphosphate in the presence of a sucrose synthase to prepare nucleotide diphosphate to which glucose is bonded, and
   (2) reacting the nucleotide diphosphate to which glucose is bonded with stevioside in the presence of a glycosyltransferase to prepare rebaudioside A,
   wherein the sucrose synthase comprises the sequence of SEQ ID NO:3,
   wherein the glycosyltransferase comprises the sequence of SEQ ID NO:4, and
   wherein the reaction system pH is in the range of pH 5.5 to 11.0.

2. The method for preparing rebaudioside A from stevioside according to claim 1, wherein the reaction system temperature is 20° C. to 60° C., and the reaction system pH is in the range of pH 7 o pH 8.

3. The method for preparing rebaudioside A from stevioside according to claim 1, wherein the sucrose synthase and the glycosyltransferase are independently produced from recombinant *Escherichia coli*, *Bacillus*, yeast, Corynebacterium or *Agrobacterium*.

4. The method for preparing rebaudioside A from stevioside according to claim 3, wherein the sucrose synthase and the glycosyltransferase are purified sucrose synthase and purified glycosyltransferase, respectively.

* * * * *

SEQUENCE LISTING

<160> NUMBER OF SEQ ID NOS: 10

<210> SEQ ID NO 1
<211> LENGTH: 2427
<212> TYPE: DNA
<213> ORGANISM: Oryza sativa

<400> SEQUENCE: 1

| | | | | | |
|---|---|---|---|---|---|
| atggctgcca | agctagctcg | cctccacagt | ctccgcgaac | gcctcggtgc | caccttctcg | 60 |
| tctcatccca | atgagttgat | tgcactcttc | tctaggtatg | ttaaccaggg | aaagggaatg | 120 |
| ctccagcgtc | accagctgct | tgcggagttc | gatgccttga | tcgaagctga | caaagagaaa | 180 |
| tatgctccct | ttgaagacat | tctccgggct | gctcaggaag | ccattgtgct | gccgccctgg | 240 |
| gttgcactgg | ccatcaggcc | aaggcctggt | gtctgggact | acattcgggt | gaatgtaagt | 300 |
| gagttggcag | tggaagagct | gagtgtttct | gagtacttgg | cattcaagga | acagcttgtt | 360 |
| gatggacaca | ccaacagcaa | ctttgttctt | gagcttgatt | ttgagccctt | caatgcctcc | 420 |
| ttcccgcgcc | cgtccatgtc | caagtccatc | ggaaatgggg | tgcagttcct | taaccgtcac | 480 |
| ctgtcgtcca | agttgttcca | ggacaaggag | agcctctacc | ccttgctgaa | cttcctgaaa | 540 |
| gcccataacc | acaagggcac | gacaatgatg | ctgaatgaca | gaattcagag | ccttcgtggg | 600 |
| ctccaatcat | cccttagaaa | ggcagaagaa | tatctgatgg | gcattcctca | agacacgccc | 660 |
| tactcggagt | tcaaccacag | gttccaagag | ctcggtttgg | agaaggggttg | gggtgactgt | 720 |
| gcaaagcgtg | tgcttgacac | catccacttg | cttcttgacc | ttcttgaggc | ccctgatccg | 780 |
| gccaacttgg | agaagttcct | tggaactatt | ccaatgatgt | tcaatgttgt | tatcctgtct | 840 |
| ccgcatggat | actttgccca | atccaatgtg | ttgggatacc | ctgatactgg | tggtcaggtt | 900 |
| gtgtacattt | tggaccaagt | ccgcgctttg | gagaatgaga | tgcttttgag | gatcaagcag | 960 |
| caaggccttg | atatcacacc | taagatcctc | attgtaacca | ggctgttgcc | tgatgctgtt | 1020 |
| ggtactacat | gcggccagcg | tgtggagaag | gttattggaa | ctgagcacac | tgacattctt | 1080 |
| cgtgttccat | tcaggagtga | aatggtatc | ctccgcaagt | ggatctcccg | ttttgatgtc | 1140 |
| tggccattcc | tggaaacata | cactgaggat | gttgcaaacg | aaattatgag | ggaaatgcaa | 1200 |
| gccaaacctg | atctcatcat | tggcaattac | agtgatggaa | accttgttgc | cactctgctg | 1260 |
| gctcacaaat | taggagttac | ccagtgtacc | attgctcatg | ccttggagaa | aaccaaatac | 1320 |
| cccaactcag | acatatactt | ggacaagttt | gacagccagt | accacttctc | atgccaattc | 1380 |
| actgctgatc | ttatcgccat | gaatcacact | gatttcatca | tcaccagtac | attccaagaa | 1440 |
| attgctggaa | gcaaggacac | tgtggggcag | tatgaatcac | acattgcatt | cacccttcct | 1500 |
| gggctttacc | gagttgtgca | tggcatagat | gtttttgatc | ccaagttcaa | cattgtctct | 1560 |
| cctggagctg | acatgagtgt | ctacttcccg | tacaccgagg | ctgacaagag | gctcactgct | 1620 |
| ttccaccctg | aaattgagga | gcttctctac | agtgaagtcg | agaacgatga | cacaagtttt | 1680 |
| gtattgaagg | acaagaacaa | gccaatcatc | ttctccatgg | ctcgtcttga | ccgagtgaag | 1740 |
| aacatgacag | gtctggttga | gatgtatggt | aagaatgcac | atctcaggga | tttggcaaac | 1800 |
| cttgtgattg | tttgtggtga | ccacggcaat | cagtccaagg | acaggaggga | gcaggctgag | 1860 |
| ttcaagaaga | tgtacggtct | cattgaccag | tacaagttga | aggggcatat | ccgctggatc | 1920 |
| tcagctcaga | tgaaccgtgt | tcgtaacggg | gagttgtacc | gatacatttg | tgacaccaag | 1980 |
| ggagtctttg | tccagcctgc | attctatgaa | gcgtttggtc | tgactgtcat | cgaagccatg | 2040 |
| acatgtggtt | tgccaacaat | cgcaacatgc | catggtggcc | ctgctgagat | tattgttgat | 2100 |

```
ggggtgtctg gtctgcacat tgatccttac cacagtgaca aggctgctga tatcttggtc    2160
aacttctttg agaagtgcaa gcaggattca acctactggg acaatatttc acagggaggt    2220
ctgcagagga tttacgagaa gtacacctgg aagctgtact ctgagaggct gatgaccttg    2280
actggtgtat acggattctg gaagtacgta agcaacttg agaggcgcga gactcgccgt    2340
tacattgaga tgttctatgc tctgaaatac cgcagcctgg ccagcgccgt cccattggct    2400
gtcgatggag agagcacatc caagtaa                                         2427

<210> SEQ ID NO 2
<211> LENGTH: 1377
<212> TYPE: DNA
<213> ORGANISM: Stevia rebaudiana

<400> SEQUENCE: 2
atggaaaata aaacggagac caccgttcgc cggcgccgga gaataatatt attcccggta      60
ccatttcaag gccacattaa cccaattctt cagctagcca atgtgttgta ctctaaagga     120
ttcagtatca ccatctttca caccaacttc aacaaaccca aacatctaa ttaccctcac      180 ttcactttca gattcatcct cgacaacgac ccacaagacg aacgcatttc caatctaccg     240
actcatggtc cgctcgctgg tatgcggatt ccgattatca cgaacacgg agctgacgaa     300 ttacgacgcg aactggaact gttgatgtta gcttctgaag aagatgaaga ggtatcgtgt     360
ttaatcacgg atgctctttg gtacttcgcg caatctgttg ctgacagtct taacctccga     420
cggcttgttt tgatgacaag cagcttgttt aattttcatg cacatgtttc acttcctcag     480
tttgatgagc ttggttacct cgatcctgat gacaaaaccc gtttggaaga caagcgagt      540 gggtttccta tgctaaaagt gaaagacatc aagtctgcgt attcgaactg gcaaatactc     600
aaagagatat tagggaagat gataaaacaa acaaaagcat cttcaggagt catctggaac     660
tcatttaagg aactcgaaga gtctgagctc gaaactgtta ccgtgagat cccggctcca     720 agtttcttga taccactccc caagcatttg acagcctctt ccagcagctt actagaccac     780
gatcgaaccg ttttcaatg gttagaccaa caaccgccaa gttcggtact gtatgttagt     840
tttggtagta ctagtgaagt ggatgagaaa gatttcttgg aaatagctcg tgggttggtt     900
gatagcaagc agtcgttttt atgggtggtt cgacctgggt ttgtcaaggg ttcgacgtgg     960
gtcgaaccgt tgccagatgg gttcttgggt gaaagaggac gtattgtgaa atgggttcca     1020
cagcaagaag tgctagctca tggagcaata ggcgcattct ggactcatag cggatggaac     1080
tctacgttga aaagcgtttg tgaaggtgtt cctatgattt tctcggattt tgggctcgat     1140
caaccgttga atgctagata catgagtgat gttttgaagg tagggtgta tttggaaaat      1200 gggtgggaaa gaggagagat agcaaatgca ataagaagag ttatggtgga tgaagaagga     1260
gaatacatta gacagaatgc aagagttttg aaacaaaagg cagatgtttc tttgatgaag     1320
ggtggttcgt cttacgaatc attagagtct ctagtttctt acatttcatc gttgtaa        1377

<210> SEQ ID NO 3
<211> LENGTH: 808
<212> TYPE: PRT
<213> ORGANISM: Oryza sativa

<400> SEQUENCE: 3

Met Ala Ala Lys Leu Ala Arg Leu His Ser Leu Arg Glu Arg Leu Gly
1               5                   10                  15

Ala Thr Phe Ser Ser His Pro Asn Glu Leu Ile Ala Leu Phe Ser Arg
```

```
            20                  25                  30
Tyr Val Asn Gln Gly Lys Gly Met Leu Gln Arg His Gln Leu Leu Ala
                35                  40                  45
Glu Phe Asp Ala Leu Ile Glu Ala Asp Lys Glu Lys Tyr Ala Pro Phe
            50                  55                  60
Glu Asp Ile Leu Arg Ala Ala Gln Glu Ala Ile Val Leu Pro Pro Trp
65                  70                  75                  80
Val Ala Leu Ala Ile Arg Pro Arg Pro Gly Val Trp Asp Tyr Ile Arg
                85                  90                  95
Val Asn Val Ser Glu Leu Ala Val Glu Glu Leu Ser Val Ser Glu Tyr
                100                 105                 110
Leu Ala Phe Lys Glu Gln Leu Val Asp Gly His Thr Asn Ser Asn Phe
                115                 120                 125
Val Leu Glu Leu Asp Phe Glu Pro Phe Asn Ala Ser Phe Pro Arg Pro
            130                 135                 140
Ser Met Ser Lys Ser Ile Gly Asn Gly Val Gln Phe Leu Asn Arg His
145                 150                 155                 160
Leu Ser Ser Lys Leu Phe Gln Asp Lys Glu Ser Leu Tyr Pro Leu Leu
                165                 170                 175
Asn Phe Leu Lys Ala His Asn His Lys Gly Thr Thr Met Met Leu Asn
                180                 185                 190
Asp Arg Ile Gln Ser Leu Arg Gly Leu Gln Ser Ser Leu Arg Lys Ala
                195                 200                 205
Glu Glu Tyr Leu Met Gly Ile Pro Gln Asp Thr Pro Tyr Ser Glu Phe
            210                 215                 220
Asn His Arg Phe Gln Glu Leu Gly Leu Glu Lys Gly Trp Gly Asp Cys
225                 230                 235                 240
Ala Lys Arg Val Leu Asp Thr Ile His Leu Leu Leu Asp Leu Leu Glu
                245                 250                 255
Ala Pro Asp Pro Ala Asn Leu Glu Lys Phe Leu Gly Thr Ile Pro Met
                260                 265                 270
Met Phe Asn Val Val Ile Leu Ser Pro His Gly Tyr Phe Ala Gln Ser
            275                 280                 285
Asn Val Leu Gly Tyr Pro Asp Thr Gly Gly Gln Val Val Tyr Ile Leu
            290                 295                 300
Asp Gln Val Arg Ala Leu Glu Asn Glu Met Leu Leu Arg Ile Lys Gln
305                 310                 315                 320
Gln Gly Leu Asp Ile Thr Pro Lys Ile Leu Ile Val Thr Arg Leu Leu
                325                 330                 335
Pro Asp Ala Val Gly Thr Thr Cys Gly Gln Arg Val Glu Lys Val Ile
                340                 345                 350
Gly Thr Glu His Thr Asp Ile Leu Arg Val Pro Phe Arg Ser Glu Asn
                355                 360                 365
Gly Ile Leu Arg Lys Trp Ile Ser Arg Phe Asp Val Trp Pro Phe Leu
            370                 375                 380
Glu Thr Tyr Thr Glu Asp Val Ala Asn Glu Ile Met Arg Glu Met Gln
385                 390                 395                 400
Ala Lys Pro Asp Leu Ile Ile Gly Asn Tyr Ser Asp Gly Asn Leu Val
                405                 410                 415
Ala Thr Leu Leu Ala His Lys Leu Gly Val Thr Gln Cys Thr Ile Ala
                420                 425                 430
His Ala Leu Glu Lys Thr Lys Tyr Pro Asn Ser Asp Ile Tyr Leu Asp
                435                 440                 445
```

Lys Phe Asp Ser Gln Tyr His Phe Ser Cys Gln Phe Thr Ala Asp Leu
450                 455                 460

Ile Ala Met Asn His Thr Asp Phe Ile Ile Thr Ser Thr Phe Gln Glu
465                 470                 475                 480

Ile Ala Gly Ser Lys Asp Thr Val Gly Gln Tyr Glu Ser His Ile Ala
                485                 490                 495

Phe Thr Leu Pro Gly Leu Tyr Arg Val Val His Gly Ile Asp Val Phe
            500                 505                 510

Asp Pro Lys Phe Asn Ile Val Ser Pro Gly Ala Asp Met Ser Val Tyr
        515                 520                 525

Phe Pro Tyr Thr Glu Ala Asp Lys Arg Leu Thr Ala Phe His Pro Glu
    530                 535                 540

Ile Glu Glu Leu Leu Tyr Ser Glu Val Glu Asn Asp Glu His Lys Phe
545                 550                 555                 560

Val Leu Lys Asp Lys Asn Lys Pro Ile Ile Phe Ser Met Ala Arg Leu
                565                 570                 575

Asp Arg Val Lys Asn Met Thr Gly Leu Val Glu Met Tyr Gly Lys Asn
            580                 585                 590

Ala His Leu Arg Asp Leu Ala Asn Leu Val Ile Val Cys Gly Asp His
        595                 600                 605

Gly Asn Gln Ser Lys Asp Arg Glu Glu Gln Ala Glu Phe Lys Lys Met
    610                 615                 620

Tyr Gly Leu Ile Asp Gln Tyr Lys Leu Lys Gly His Ile Arg Trp Ile
625                 630                 635                 640

Ser Ala Gln Met Asn Arg Val Arg Asn Gly Glu Leu Tyr Arg Tyr Ile
                645                 650                 655

Cys Asp Thr Lys Gly Val Phe Val Gln Pro Ala Phe Tyr Glu Ala Phe
            660                 665                 670

Gly Leu Thr Val Ile Glu Ala Met Thr Cys Gly Leu Pro Thr Ile Ala
        675                 680                 685

Thr Cys His Gly Gly Pro Ala Glu Ile Ile Val Asp Gly Val Ser Gly
    690                 695                 700

Leu His Ile Asp Pro Tyr His Ser Asp Lys Ala Ala Asp Ile Leu Val
705                 710                 715                 720

Asn Phe Phe Glu Lys Cys Lys Gln Asp Ser Thr Tyr Trp Asp Asn Ile
                725                 730                 735

Ser Gln Gly Gly Leu Gln Arg Ile Tyr Glu Lys Tyr Thr Trp Lys Leu
            740                 745                 750

Tyr Ser Glu Arg Leu Met Thr Leu Thr Gly Val Tyr Gly Phe Trp Lys
        755                 760                 765

Tyr Val Ser Asn Leu Glu Arg Arg Glu Thr Arg Arg Tyr Ile Glu Met
    770                 775                 780

Phe Tyr Ala Leu Lys Tyr Arg Ser Leu Ala Ser Ala Val Pro Leu Ala
785                 790                 795                 800

Val Asp Gly Glu Ser Thr Ser Lys
                805

<210> SEQ ID NO 4
<211> LENGTH: 458
<212> TYPE: PRT
<213> ORGANISM: Stevia rebaudiana

<400> SEQUENCE: 4

Met Glu Asn Lys Thr Glu Thr Thr Val Arg Arg Arg Arg Arg Ile Ile

```
  1               5                   10                  15
Leu Phe Pro Val Pro Phe Gln Gly His Ile Asn Pro Ile Leu Gln Leu
                20                  25                  30

Ala Asn Val Leu Tyr Ser Lys Gly Phe Ser Ile Thr Ile Phe His Thr
                35                  40                  45

Asn Phe Asn Lys Pro Lys Thr Ser Asn Tyr Pro His Phe Thr Phe Arg
 50                  55                  60

Phe Ile Leu Asp Asn Asp Pro Gln Asp Glu Arg Ile Ser Asn Leu Pro
 65                  70                  75                  80

Thr His Gly Pro Leu Ala Gly Met Arg Ile Pro Ile Ile Asn Glu His
                 85                  90                  95

Gly Ala Asp Glu Leu Arg Arg Glu Leu Glu Leu Leu Met Leu Ala Ser
                100                 105                 110

Glu Glu Asp Glu Glu Val Ser Cys Leu Ile Thr Asp Ala Leu Trp Tyr
                115                 120                 125

Phe Ala Gln Ser Val Ala Asp Ser Leu Asn Leu Arg Arg Leu Val Leu
                130                 135                 140

Met Thr Ser Ser Leu Phe Asn Phe His Ala His Val Ser Leu Pro Gln
145                 150                 155                 160

Phe Asp Glu Leu Gly Tyr Leu Asp Pro Asp Asp Lys Thr Arg Leu Glu
                165                 170                 175

Glu Gln Ala Ser Gly Phe Pro Met Leu Lys Val Lys Asp Ile Lys Ser
                180                 185                 190

Ala Tyr Ser Asn Trp Gln Ile Leu Lys Glu Ile Leu Gly Lys Met Ile
                195                 200                 205

Lys Gln Thr Lys Ala Ser Ser Gly Val Ile Trp Asn Ser Phe Lys Glu
                210                 215                 220

Leu Glu Glu Ser Glu Leu Glu Thr Val Ile Arg Glu Ile Pro Ala Pro
225                 230                 235                 240

Ser Phe Leu Ile Pro Leu Pro Lys His Leu Thr Ala Ser Ser Ser Ser
                245                 250                 255

Leu Leu Asp His Asp Arg Thr Val Phe Gln Trp Leu Asp Gln Gln Pro
                260                 265                 270

Pro Ser Ser Val Leu Tyr Val Ser Phe Gly Ser Thr Ser Glu Val Asp
                275                 280                 285

Glu Lys Asp Phe Leu Glu Ile Ala Arg Gly Leu Val Asp Ser Lys Gln
                290                 295                 300

Ser Phe Leu Trp Val Val Arg Pro Gly Phe Val Lys Gly Ser Thr Trp
305                 310                 315                 320

Val Glu Pro Leu Pro Asp Gly Phe Leu Gly Glu Arg Gly Arg Ile Val
                325                 330                 335

Lys Trp Val Pro Gln Gln Glu Val Leu Ala His Gly Ala Ile Gly Ala
                340                 345                 350

Phe Trp Thr His Ser Gly Trp Asn Ser Thr Leu Glu Ser Val Cys Glu
                355                 360                 365

Gly Val Pro Met Ile Phe Ser Asp Phe Gly Leu Asp Gln Pro Leu Asn
                370                 375                 380

Ala Arg Tyr Met Ser Asp Val Leu Lys Val Gly Val Tyr Leu Glu Asn
385                 390                 395                 400

Gly Trp Glu Arg Gly Glu Ile Ala Asn Ala Ile Arg Arg Val Met Val
                405                 410                 415

Asp Glu Glu Gly Glu Tyr Ile Arg Gln Asn Ala Arg Val Leu Lys Gln
                420                 425                 430
```

Lys Ala Asp Val Ser Leu Met Lys Gly Gly Ser Ser Tyr Glu Ser Leu
        435                 440                 445

Glu Ser Leu Val Ser Tyr Ile Ser Ser Leu
    450                 455

<210> SEQ ID NO 5
<211> LENGTH: 23
<212> TYPE: DNA
<213> ORGANISM: Artificial Sequence
<220> FEATURE:
<223> OTHER INFORMATION: PCR primer

<400> SEQUENCE: 5
catatggctg ccaagctagc tcg                                            23

<210> SEQ ID NO 6
<211> LENGTH: 26
<212> TYPE: DNA
<213> ORGANISM: Artificial Sequence
<220> FEATURE:
<223> OTHER INFORMATION: PCR primer

<400> SEQUENCE: 6
aagcttttac ttgatgtgc tctctc                                          26

<210> SEQ ID NO 7
<211> LENGTH: 20
<212> TYPE: DNA
<213> ORGANISM: Artificial Sequence
<220> FEATURE:
<223> OTHER INFORMATION: PCR primer

<400> SEQUENCE: 7
catatggaaa ataaaacgga                                                20

<210> SEQ ID NO 8
<211> LENGTH: 26
<212> TYPE: DNA
<213> ORGANISM: Artificial Sequence
<220> FEATURE:
<223> OTHER INFORMATION: PCR primer

<400> SEQUENCE: 8
aagcttttac ttgatgtgc tctctc                                          26

<210> SEQ ID NO 9
<211> LENGTH: 377
<212> TYPE: DNA
<213> ORGANISM: Oryza sativa

<400> SEQUENCE: 9
tgccaacaat cgcaacatgc catggtggcc ctgctgagat tattgttgat ggggtgtctg     60
gtctgcacat tgatccttac cacagtgaca aggctgctga tatcttggtc aacttctttg    120
agaagtgcaa gcaggattca acctactggg acaatatttc acagggaggt ctgcagagga    180
tttacgagaa gtacacctgg aagctgtact ctgagaggct gatgaccttg actggtgtat    240
acggattctg gaagtacgta agcaaccttg agaggcgcga gactcgccgt tacattgaga    300
tgttctatgc tctgaaatac cgcagcctgg ccagcgccgt cccattggct gtcgatggag    360
agagcacatc caagtaa                                                   377

<210> SEQ ID NO 10

```
<211> LENGTH: 352
<212> TYPE: DNA
<213> ORGANISM: Stevia rebaudiana

<400> SEQUENCE: 10
agaagtgcta gctcatggag caataggcgc attctggact catagcggat ggaactctac      60
gttggaaagc gtttgtgaag gtgttcctat gattttctcg gattttgggc tcgatcaacc     120
gttgaatgct agatacatga gtgatgtttt gaaggtaggg gtgtatttgg aaaatgggtg     180
ggaaagagga gagatagcaa atgcaataag aagagttatg gtggatgaag aaggagaata     240
cattagacag aatgcaagag ttttgaaaca aaaggcagat gtttctttga tgaagggtgg     300
ttcgtcttac gaatcattag agtctctagt ttcttacatt tcatcgttgt aa             352
```